US006892727B2

(12) United States Patent
Myrman

(10) Patent No.: US 6,892,727 B2
(45) Date of Patent: *May 17, 2005

(54) DEVICE CONSTITUTING A POWDER AIR-RAZOR

(75) Inventor: Mattias Myrman, Stockholm (SE)

(73) Assignee: Mederio AG, Hergiswil (CH)

(*) Notice: Subject to any disclaimer, the term of this patent is extended or adjusted under 35 U.S.C. 154(b) by 358 days.

This patent is subject to a terminal disclaimer.

(21) Appl. No.: 10/134,474

(22) Filed: Apr. 30, 2002

(65) Prior Publication Data
US 2003/0192538 A1 Oct. 16, 2003

(30) Foreign Application Priority Data
Apr. 12, 2002 (SE) .............................................. 0201124

(51) Int. Cl.[7] ............................................... A61M 15/00

(52) U.S. Cl. ............................. 128/203.15; 128/203.19

(58) Field of Search ....................... 128/200.21, 200.24, 128/200.23, 203.12, 202.21, 203.13, 203.14, 203.15, 203.18, 203.19, 203.21, 204.11–204.13; 604/58; 424/46; 222/146.1, 146.3, 190

(56) References Cited

U.S. PATENT DOCUMENTS

| | | | | | |
|---|---|---|---|---|---|
| 5,113,855 | A | | 5/1992 | Newhouse | |
| 5,161,524 | A | | 11/1992 | Evans | |
| 5,349,945 | A | | 9/1994 | Wass et al. | |
| 5,388,572 | A | | 2/1995 | Mulhauser et al. | |
| 5,408,994 | A | | 4/1995 | Wass et al. | |
| 5,469,843 | A | | 11/1995 | Hodson | |
| 5,655,523 | A | | 8/1997 | Hodson et al. | |
| 5,694,920 | A | | 12/1997 | Abrams et al. | |
| 5,823,182 | A | * | 10/1998 | Van Oort | 128/203.12 |
| 5,829,434 | A | * | 11/1998 | Ambrosio et al. | 128/203.15 |
| 5,952,008 | A | * | 9/1999 | Backstrom et al. | 424/499 |
| 6,074,688 | A | * | 6/2000 | Pletcher et al. | 427/2.14 |
| 6,245,339 | B1 | * | 6/2001 | Van Oort et al. | 424/400 |
| 6,298,847 | B1 | * | 10/2001 | Datta et al. | 128/203.15 |
| 6,397,840 | B1 | * | 6/2002 | Chrai et al. | 128/202.25 |
| 6,422,236 | B1 | * | 7/2002 | Nilsson et al. | 128/203.15 |
| 6,439,227 | B1 | * | 8/2002 | Myrman et al. | 128/200.14 |
| 6,524,557 | B1 | * | 2/2003 | Backstrom et al. | 424/46 |
| 6,591,833 | B2 | * | 7/2003 | Datta et al. | 128/203.15 |
| 6,651,341 | B1 | * | 11/2003 | Myrman et al. | 30/2 |
| 6,668,826 | B1 | * | 12/2003 | Myrman | 128/203.15 |
| 6,681,768 | B2 | * | 1/2004 | Haaije de Boer et al. | 128/203.15 |
| 2004/0069303 | A1 | * | 4/2004 | Brown et al. | 128/203.15 |

FOREIGN PATENT DOCUMENTS

| | | | |
|---|---|---|---|
| EP | 0 069 715 | A1 | 1/1983 |
| EP | 0 414 536 | A2 | 2/1991 |
| WO | 01/34233 | A1 | 5/2001 |
| WO | 02/24264 | A1 | 3/2002 |

* cited by examiner

*Primary Examiner*—Henry Bennett
*Assistant Examiner*—Teena Mitchell
(74) *Attorney, Agent, or Firm*—Young & Thompson

(57) ABSTRACT

A device and an arrangement are disclosed, which create a powder Air-razor, which into an inhalation air volume de-aggregates and disperses a finely divided medication powder. The powder is generally loaded onto a dosing member intended for use with an inhaler. By sucking air through a mouthpiece connected to a nozzle, particles of the load of powder are gradually de-aggregated, dispersed and continuously released into the sucked air during a defined interval. The gradual de-aggregation and dispersal of the medication powder is generated by a relative motion introduced between the nozzle and the dosing member. The powder is generally loaded onto a larger area than the area of the air nozzle inlet. The nozzle may be positioned outside the dose area until an air stream has begun to flow into the nozzle by suction of air in an inhaling operation.

32 Claims, 12 Drawing Sheets

311 (Laminar flow)
310 (Turbulent flow)
U(y)

Fig. 13

Total number of particles dispersed in air flow as a function of elapsed time

DEVICE CONSTITUTING A POWDER AIR-RAZOR

TECHNICAL FIELD

The present invention relates to a device and an arrangement constituting a powder Air-razor for de-aggregating and into air dispersing finely divided dry medication powder, made available for a release and intended for inhalation through a dry powder inhaler device.

BACKGROUND

The dosing of drugs is carried out in a number of different ways in the medical service today. Within health-care, there is a rapidly growing interest in administering locally or systemically acting medication in prescribed doses of powder directly to the airways and lungs of a patient by means of an inhaler in order to obtain an effective, quick and user-friendly administration of such drugs.

A dry powder inhaler, DPI, represents a device intended for administration of doses of powder into the deep and/or upper lung airways by oral inhalation. However, deep lung deposition of medicament is a more difficult proposition and has only recently come into focus. Most inhalers on the market today are designed for treatment of ailments in the airways or local lung, like asthma, where the objective often is local, not deep lung, deposition. When the objective is a systemic delivery of the medication, then a deep lung deposition of the powder is preferred and usually necessary for maximum efficiency. The deep lung is defined as the peripheral lung and alveoli, where direct transport of a substance to the blood can take place. If a particle is to reach into the deep lung the aerodynamic particle size should typically be less than 3 $\mu$m, and for a local lung deposition, typically about 5 $\mu$m. Larger particle sizes will easily stick in the mouth and throat. Thus, regardless of whether the objective is a local or systemic delivery of a drug, it is important to keep the particle size distribution of the dose within tight limits to ensure that a high percentage of the dose is actually deposited where it will be most effective.

Particle size is especially important for a successful delivery to the deep lung upon inhalation. Furthermore, for optimal results, the inspiration must take place in a calm manner to decrease air speed and thereby reduce deposition by impaction in the upper respiratory tracts. The advantages of using the inhalation power of the user to full potential in a prolonged, continuous dose delivery interval within the inhalation cycle is disclosed in our Swedish Patent no. SE 9904081-8 (WO 01/34233 A1), which is hereby incorporated herein by reference, in its entirety. The patent presents several devices for efficient distribution of pharmaceutical compositions in fine powder form in the inspiration air, without using other sources of energy than the power of the air in the user's inhalation.

Powders for inhalation have a tendency of aggregating, in other words to clod or to form smaller or larger lumps of particles, which then have to be de-aggregated before the particles enter into the mouth of the user. De-aggregating is defined as breaking up aggregated powder by introducing energy; e.g. electrical, mechanical, pneumatic or aerodynamic energy. To succeed with systemic delivery of medication powders by inhalation to the deep lung, it is important to achieve a high degree of de-aggregation of the medication powder in the inhaled air. In most cases, treatment of a patient is not a single occurrence, but has to be repeated and in some chronic cases, treatment has to be on a continuous basis. In all cases, de-aggregation must be very repeatable and dosing must be kept within tight tolerances from one administration to the next.

A majority of dry powder inhalers of today presents rather moderate deaggregation capacity. Current inhalation devices intended for asthma and other lung diseases normally deliver the dispensed drug particles in a larger size range than optimal for deep lung deposition. This is often caused by inadequate de-aggregation of powder particle aggregates with a primary particle size in the range 2–3 $\mu$m. Thus, the inhaled dose consists of aggregates of smaller particles. This entails several disadvantages:

The uniformity of aerodynamic particle size distribution between different doses may vary considerably, because the de-aggregation is sensitive to slight differences in inspiration conditions from one inhalation to the next.

Particle size distribution of the delivered dose may have a tail of big aggregates, which will deposit in the mouth and upper airways.

Retention of the substance in the inhaler may vary with the aerodynamic particle size distribution and may hence be difficult to control and predict.

Thus, for a consistent, predictable and repeatable delivery of medicaments to the lungs there is a need of a de-aggregating system capable of producing reproducibly a very high degree of de-aggregation of the dry powder medicament. This is especially true for systemically acting drugs, where a deep lung deposition is normally required. In addition, for locally acting medicaments, where usually a local lung deposition is preferred, a high degree of de-aggregation of the medication powder is an advantage. Preferably, the de-aggregating system ought to be insensitive as far as possible to the inhalation effort produced by the user, such that the delivered aerodynamic particle size distribution in the inhaled air is independent of the inhalation effort. The average aerodynamic particle size, which influences the deposition pattern in the lungs, can be controlled by controlling the primary particle size distribution of the particles constituting the powder.

Introducing special devices as for example spacers and/or external sources of energy to amplify the inhalation energy provided by the user during the act of inhalation are common methods in prior art inhalers for improving the performance in terms of de-aggregation and dosing predictability and repeatability. The addition of external sources of energy leads to more complex and expensive inhalers than necessary, besides increasing the demands put on the user in maintaining the inhaler.

Over the years, many methods and devices have been tried in order to improve the performance of drug delivery systems based on inhalation. For instance, U.S. Pat. No. 480,505, dated as early as Aug. 9, 1892, describes a nasal respirator device, including reticulated material and adapted to receiving a porous medium impregnated with medicine. Nets, screens or membranes with interstices are well known to a person skilled in the art, as components in many inhaler designs, either as carriers of drugs or elements to facilitate the release of the dose to a user. An example of a prior art inhaler device using a perforated membrane as a dispensing element for an active compound of medicament is disclosed in a European patent EP 0 069 715 B1 with priority date Aug. 7, 1981. The patent teaches an inhaler comprising a nozzle, an air conduit and a displaceable dispensing element in the form of a perforated membrane, for dispensing the medicament from a storage chamber into the air conduit. Dry powder inhaler medicament carriers with interstices for enhancement of de-aggregation of a powder dose are dealt with in several later documents e.g. U.S. Pat. Nos. 5,388, 572; 5,388,573; 5,460,173; 5,647,347; 5,823,182; 6,245,339 B1 and WIPO publication Nos. WO94/20164; WO98/04308. The carriers and methods, taught in the referred documents, are characterized in that the powdered medicament is impregnated or embedded in and across interstices at spaced locations in the carrier, thus forming one or more doses of medicament. A dose is then put in a flow channel connected to a mouthpiece. As the user inhales through the mouthpiece the created air stream forces the aggregated dry powder particles of the dose loaded onto or into the carrier to be released into air and de-aggregated by the shearing force of the air as it passes through the interstices and past the aggregated powder particles. Thus, a main purpose of the net or screen type of carrier presented in the referred documents is to facilitate de-aggregation of the dose. However, examples in some of the documents show pressure chambers or similar means for creating a high-pressure air pulse, 70 psig (=490 kPa) in one case, necessary to blow the dose off the carrier. A pressure of 70 psig is about 100 times higher than the pressure drop produced by the inhalation of a user. A normal inspiration by an adult produces about 5 kPa and an external energy source is therefore necessary in order to produce the air pulse. The suggested methods seem to be limited in terms of dose mass, only being suitable for rather small doses. The teachings also suggest using ordered mixtures of active substance and some excipient, to further improve de-aggregation, which further limits the active medicament mass in the dose.

Another example of an inhalation device addressing the problem of de-aggregation is disclosed in U.S. Pat. No. 5,694,920 and further improvements of the inhaler are disclosed in U.S. Pat. Nos. 6,026,809 and 6,142,146. The inventions teach that de-aggregation of a medication powder may be provided by a vibrator, which directly or indirectly imparts mechanical energy of suitable frequency and power to the powder. The powder is thus fluidized and de-aggregated. Particles of a size suitable for inhalation are then lifted out from the fluidized powder and introduced in an air stream by an electric field of suitable strength established across the air stream. The particles are then delivered to a user by the air stream. Clearly, it is necessary to provide external power in electro-mechanical form to achieve de-aggregation, which still seems to be only partially successful.

Prior art methods achieving a high de-aggregation and dispersal into air of a dry medication powder seem to require high levels of de-aggregating power, which lead to more or less complicated inhaler designs.

SUMMARY

The present invention discloses a device and an arrangement for efficient de-aggregation and dispersal into air of a finely divided medication powder. In contrast to prior art the present invention does not require other sources of energy besides the power of the inhalation effort by the user to produce a very high degree of de-aggregation and efficient dispersal into air of a dry powder.

A device and an arrangement are disclosed, which provide a powder Air-razor for de-aggregating and into air dispersing a finely divided medication powder. Utilizing an effort of sucking air through a nozzle, the particles in the powder, made available to the nozzle, are gradually de-aggregated and dispersed into a stream of air entering the nozzle. The gradual de-aggregation and dispersal will be produced by a relative motion introduced between the nozzle and the powder. In a preferred embodiment the powder is deposited onto a substrate, the accumulated powder occupying a larger area than the area of the nozzle inlet. The nozzle is preferably positioned outside the powder area, not accessing the powder by the relative motion until the air stream into the nozzle, created by the suction, has passed a threshold flow speed. Coincidental with the application of the suction or shortly afterwards the relative motion will begin such that the nozzle traverses the load of powder gradually. The high velocity air going into the nozzle inlet provides plenty of shearing stress and impact energy as the flowing air hits the leading point of the border of the contour of the accumulated powder. This powder Air-razor effect, created by the shearing stress and the impact of the air stream, is so powerful that the particles in the particle aggregates in the powder adjacent to the inlet of the moving nozzle are released, de-aggregated to a very high degree as well as dispersed and subsequently entrained in the created air stream going through the nozzle.

A powder Air-razor device for de-aggregating and dispersing a metered dose according to the present invention is set forth by the independent claims 1, 13, and 24 and further embodiments are defined by the dependent claims 2 to 12, 14 to 23 and 25 to 32.

SHORT DESCRIPTION OF THE DRAWINGS

The invention, together with further objects and advantages thereof, may best be understood by referring to the following detailed description taken together with the accompanying drawings, in which:

FIG. 1*a* illustrates an embodiment of the powder Air-razor device in a start position;

FIG. 1*b* illustrates an embodiment of the powder Air-razor device in a powder releasing phase;

FIG. 2*a* illustrates another embodiment of the powder Air-razor device in a start position;

FIG. 2*b* illustrates another embodiment of the powder Air-razor device in a powder releasing phase;

FIG. 3*a* illustrates yet another embodiment of the powder Air-razor device in a start position;

FIG. 3*b* illustrates yet another embodiment of the powder Air-razor device in a powder releasing phase;

FIG. 4*a* illustrates yet another embodiment of the powder Air-razor device in a start position;

FIG. 4*b* illustrates yet another embodiment of the powder Air-razor device in a powder releasing phase;

FIG. 12 illustrates fluid velocity as a function of distance to an object for laminar and turbulent flows and FIG. 13 illustrates the number of particles released into air as a function of time.

DESCRIPTION

Figure 1A:
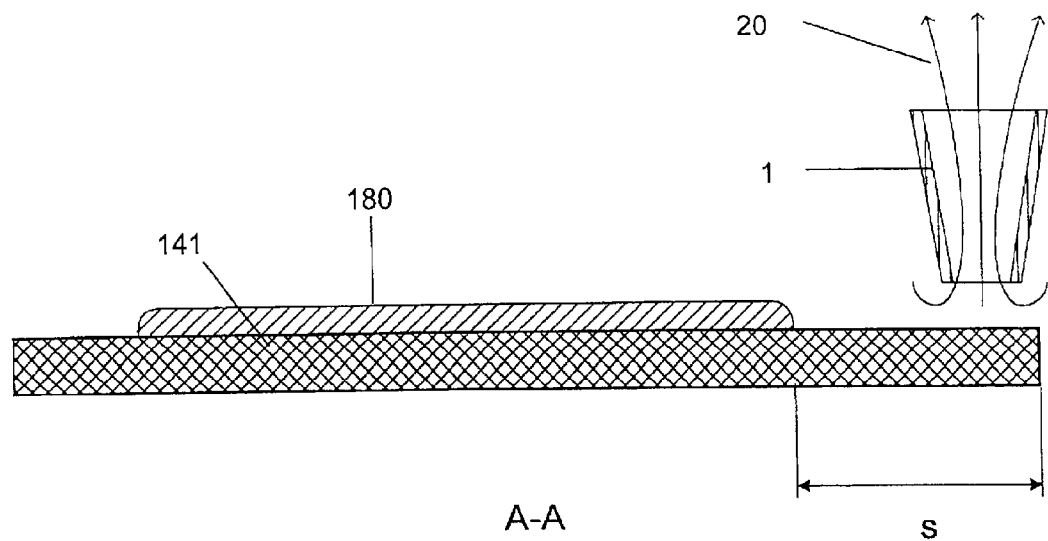

The present invention discloses a powder Air-razor device for de-aggregating and dispersing into air a dry medication powder. The invention teaches that finely divided dry medication powder may be delivered to a user with an extremely high degree of de-aggregation of the powder. The invention presents a powder Air-razor device and an arrangement to achieve the stated objective.

An important element of the Air-razor device is a relative motion between a nozzle and a powder. In the document the term "relative motion" refers to the non-airborne powder in more or less aggregated form being gradually moved, relatively speaking, by the motion into close proximity to said nozzle, where de-aggregation and dispersal into air of individual powder particles may take place, provided by the Air-razor. The term does not refer to airborne powder particles already entrained in air. Therefore, the mentioning of "motion" or "moving" in relation to "powder" refers to the contour of powder before the powder particles are released and dispersed into air.

The medication powder comprises one or more pharmacologically active substances and optionally one or more excipients. In the document the terms "powder" or "medication powder" are used to signify the substance in the form of dry powder, which is the subject of de-aggregation and dispersal into air by the disclosed invention and intended for deposition at a selected target area of a user's airways. Optional excipients may or may not de-aggregate in a similar way as the active pharmacological substance, depending on the design of the powder. For example, an ordered mixture comprises an excipient characterized by particles considerably larger than those of the pharmacologically active substance.

A preferred embodiment of the invention is illustrated in FIG. 1*a*, showing in a sectional view A—A an example of a medication powder 180 deposited onto the surface of a substrate member 141 and on the same side of the substrate member as the powder, a nozzle 1 in a starting position before the powder is released. FIG. 1*b* illustrates the nozzle moving in relation to the substrate member, showing how the powder 180 is being released, de-aggregated and dispersed into air 20 from the surface of the substrate member 141 by a stream of air hitting the powder before going into the inlet aperture of the moving nozzle, epitomizing a powder Air-razor device.

Another embodiment is illustrated in FIG. 2*a*, showing in a sectional view A—A an example of a medication powder 180 deposited onto the surface of a perforated substrate member 140 and on the same side of the substrate member as the powder, a nozzle 1 in a starting position before the powder is released. FIG. 2*b* illustrates the nozzle moving relative to the substrate, showing how the powder is being released, de-aggregated and dispersed into air 20 from the surface of the substrate member by a stream of air first going through the perforations, then via the powder and into the inlet aperture of the moving nozzle, epitomizing a powder Air-razor device.

Yet another embodiment of the powder Air-razor device is illustrated in FIG. 3*a* similar to FIG. 2*a* but with the powder 180 deposited underneath the substrate and a nozzle 1, adjacent to the upper opposite side of the substrate member 140 as the powder, in a starting position before the powder is released. FIG. 3*b* illustrates the powder as it is being released, de-aggregated and dispersed from the surface of the substrate member by a stream of air going through the perforations and into the inlet aperture of the moving nozzle, relatively speaking, on the opposite side of the substrate member as the powder; the moving nozzle thus epitomizing a powder Air-razor device. Yet another embodiment of the powder Air-razor device is illustrated in FIG. 4*a* similar to FIGS. 2*a* and 3*a* showing a medication powder deposited onto both surfaces, 180A and 180B, of a perforated substrate member 140. A nozzle 1 at side 180A is in a starting position before the powder is released. FIG. 4*b* illustrates a stream of air accessing the powder on the side 180B, then going through the perforations and accessing the powder on the side 180A before going into the inlet aperture of the nozzle, in a relative motion, epitomizing a powder Air-razor device.

FIG. 5 illustrates in a sectional view A—A a detailed example of a medication powder deposited onto the surface of a substrate member and a nozzle performing a relative motion, epitomizing a powder Air-razor device as the powder is being released, de-aggregated, dispersed and entrained in air.

FIG. 6 illustrates in a top view a substrate member 141 with a load of powder 180 onto it and a nozzle 1 with an elliptical inlet aperture 3 and in a sectional view A—A the substrate member, powder and nozzle before the nozzle 1 has begun its relative motion in the direction of the powder 180.

FIG. 7 illustrates an embodiment of a powder Air-razor device in an inhaler context, showing a dosing member 4 comprising six substrate members 140 or 141 each provided with a metered dose of powder 180. A nozzle 1, part of a suction tube 33 and a dosing member 4 with one of the substrate members 140 or 141 are in positions for releasing an amount of powder. When a spring 9 releases (release mechanism not shown here but is indicated in FIG. 9) the dosing member 4, it is put in motion bringing the substrate member 140 (141) and including the powder 180 past the nozzle 1. An airbrake 22 controls the speed of the dosing member and thereby the release interval of the powder 180, which is gradually sucked up by an air stream 20 (not illustrated) going into the nozzle 1 because of suction applied to the suction tube 33. A foil cutter 11 may optionally be positioned in front of the nozzle, such that if the dose is protected by a foil, this will be first cut open and folded away to give the nozzle full access to the powder.

FIG. 8 illustrates the powder Air-razor in action, i.e. how the powder 180, deposited onto one of the substrate members 140 or 141, is gradually accessed by the nozzle 1 and the air stream (not illustrated) as the dosing member and the suction tube 33 are put in a relative motion to each other.

FIG. 9 illustrates an embodiment of an inhaler 8 comprising a powder Air-razor device, a dosing member 4 comprising one or more substrate members 140 or 141 each provided with a metered dose of powder 180 to be administered sequentially to a user. A breath-actuation mechanism 16, lets air in and releases a catch 12 holding the dosing member (the loading and the complete releasing mechanisms are not shown) when the suction applied to a mouthpiece 19, in fluid connection with the suction tube 33, is sufficiently strong.

Theoretical Background to the Concept of a Powder Air-Razor Device

Adhesion of Particles

Particles adjacent to other particles or to a substrate member will adhere to each other. Many different types of adhesive forces will play roles in the total adhesive force between a particle and the environment, whether another particle, an aggregate of particles, a substrate member or a combination thereof. The types of adhesive forces acting on a particle can be van der Waal forces, capillary forces, electrical forces, electrostatic forces, etc. The relative strengths and ranges of these forces vary with e.g. material, environment, size and shape of the particle. The sum of all these forces acting on a particle is hereinafter referred to as an adhesive force.

De-Aggregation and Entrainment of Particles

The main objective of the Air-razor is to de-aggregate and entrain the deposited particles into the air stream. The particles may be loaded onto a substrate member in many layers in such a way that some particles are in contact with the substrate member whilst others are in contact only with other particles. A complete de-aggregation is to separate all the particles from each other. To separate a particle from its environment involves overcoming the adhesive force as well as the friction force, acting on the particle.

FIG. 11 illustrates forces acting on a particle. The force caused by airflow 303 acting on a particle 101 can be divided into two parts, drag force 305 acting parallel to the airflow, and lift force 304 acting perpendicular to the airflow. The condition for freeing the particle is in the static case that lift and drag forces exceed adhesion 301 and friction 302 forces.

In order to completely, or almost completely de-aggregate particles it is not sufficient to let a force act on the particles with enough strength for release and entrainment. If a strong force acts on an aggregate of particles, such that more or less the same force acts on all particles, the aggregate will be entrained into the airflow without de-aggregating. The condition for de-aggregation may thus be stated as: The difference in external forces acting on two particles must overcome the adhesion and friction forces holding them together. Attaining a difference in force from airflow may be done efficiently by creating shear forces, and hence the Air-razor invention makes use of high shear forces in the area of the powder deposited for instance onto a substrate member.

Shear Forces

Creating high shear forces implies creating a big velocity gradient in the flow, which is illustrated by the equation for shear stress in a fluid;

$$\tau = \mu \frac{dU(y)}{dy};$$

where $\mu$=Dynamic viscosity

U(y)=Air speed U is a function of y y=Distance from wall surface dU/dy=Velocity change per unit distance To develop high shear stress and thereby high shear forces on the particles, the main principles used in the Air-razor are:

High velocity of the air stream

Use of flow streamlines close to a wall

Use of turbulent flow (side effect from high velocity)

High Velocity Flow

High velocity flow is the basis for high shear forces (close to a wall), drag forces, lift forces and turbulence. For a given pressure drop driving airflow, the objective should be to reach maximum velocity. The theoretical maximum velocity from a certain static pressure drop can be derived from Bernoulli's streamline theorem. In reality, there will always be dissipation of energy and the velocity will not reach the levels stated by the equation, but it can be used as a limit value.

$$p + \frac{1}{2}\rho u^2 = H;$$

where p=Static pressure

ρ=Density of fluid u=Velocity

H=Constant

The equation is called Bernoulli's streamline theorem. H is a constant along a streamline for an 'idea' fluid. Hydrostatic pressure is here excluded from the equation.

The efficiency of the Air-razor method may be optimised by careful design of the geometry of involved flow elements with the aim to reach as high a velocity as possible in the de-aggregation area, but at the same time a smooth transportation of air in other areas. This will minimise the dissipative losses where not wanted and so preserve energy for use in the area adjacent to the powder. When suction is applied to a nozzle, a low-pressure develops that accelerates the air through the nozzle during a short period before a steady state condition is reached. Initially, during the start-up period as the air picks up inertia, the velocity is not high enough to generate the necessary shear forces. Preferably, during this initial period the Air-razor pauses before the powder onto a substrate member is brought adjacent to the nozzle. This ensures that the conditions for an efficient de-aggregation of the powder exist before a point at the border of the powder contour is attacked by the air stream.

Flow Close to a Wall

A high velocity flow close to a wall will create high shear forces and this is used in the present invention. The flow at zero distance from a wall is always zero. This is known as the 'No slip' condition and is true for all fluids. In a thin layer close to the wall the flow velocity will increase rapidly with the distance from the wall, and the shear stress in this boundary layer will be correspondingly high. This boundary layer can be laminar or turbulent. The velocity profile and gradient differ between turbulent and laminar boundary layers, where the higher gradients and thus shear stress exist in the turbulent layer. The Air-razor invention makes use of the concentrated flow close to the nozzle inside wall as well as the wall of the substrate member, and especially the small gap between the aperture wall on the nozzle inlet and the substrate member.

The area experiencing high shear stress is normally small in relation to the area occupied by the powder. Therefore, a relative motion between the nozzle and the powder is introduced. This allows the concentrated small area of high shear stress to traverse the entire amount of powder for instance onto a substrate member.

Turbulent Flow

FIG. 12 illustrates in form of a diagram typical velocity characteristics for laminar 311 and turbulent 310 boundary layers. The velocity gradient and so the shear stress is larger in the turbulent layer. A turbulent flow, either in a boundary layer or in a free streaming flow, is characterized by irregular flow with eddies in various sizes and frequencies. Turbulent flow fluctuates in both time and space. In any particular moment, high gradients of velocity can be seen and so it is clear that high shear stress exists in the turbulent flow away from wall surfaces. This means that particle aggregates can be de-aggregated within a turbulent air stream even after the entrainment into air of an aggregate of particles. Another advantage of turbulence depends on the fluctuations in the turbulent flow with time, which will affect the particles with a force varying in time. In fully developed turbulence, the frequency of the fluctuations will cover a large span, i.e. from low to high frequencies. Should the frequency of the varying force come close to a resonance frequency of a particle-particle system or a particle-wall system, the amplitude will grow bigger and separation may occur even though the static force is too weak for separation.

The criteria determining whether the flow is turbulent or not are Reynolds number together with the geometry of the fluid transporting channel. The absolute level of Reynolds number where transition from laminar to turbulent flow will take place depends on the surface roughness and said geometry. Keeping these constant, the value of Reynolds number will determine the nature of the flow. As seen below Reynolds number is proportional to velocity, hence the velocity has a direct influence on the turbulence.

$$R_e = \frac{U\infty L}{v};$$

where
$R_e$=Reynolds number
$U_\infty$=The free stream velocity
L=Typical length
v=Kinematical viscosity Air-Razor Movement The importance of shear forces for an efficient de-aggregation of particles and the theoretical background as to why has been discussed in the foregoing. The relative motion introduced between the nozzle and the load of powder, i.e. the substrate member normally serving as carrier, is instrumental in attaining and maintaining the desired conditions stated for de-aggregating all of a powder load and not just part of it. The main advantages given by the motion are:

During an initial acceleration phase inertia builds up giving a high velocity air flow
Shear forces close to a wall are spread over a large area
Efficient use of energy Inertia Build Up The low-pressure created by the suction through the nozzle drives air to flow in the direction of the low-pressure. Building up inertia means accelerating the mass in a system, i.e. the mass of the air itself, hence giving the desired high velocity air flow after the acceleration period. The velocity of the flow increases to a point where the flow resistance makes further increase impossible, unless the level of low-pressure is decreased, i.e. the pressure drop is increased, or the flow resistance is decreased.

Shear Force Spreading

The area for de-aggregation with high shear forces is concentrated close to the wall of the nozzle. This concentrated area is small compared to the dose area onto a substrate member, especially if the dose comprises finely divided powder of high porosity. The relative motion between the nozzle and the dose will make the small and concentrated area of high shear stress traverse over the area occupied by the dose. Depending on the actual spatial distribution of the powder in the extended dose and the distance perpendicular to the direction of the motion between the powder and the nozzle inlet aperture, it may occur that the nozzle makes contact with some of the powder. In such a case the efficiency of the Air-razor method is not detrimentally affected because of the "hoover" effect. The velocity of the airflow will not be affected by the motion of the nozzle in relation to the powder dose, because the speed of the relative motion is very much lower than the velocity of the air flow going into the nozzle inlet. However, the motion of the nozzle forcibly shifts the position of the driving low-pressure relative the contour of the dose in the direction of the motion. Thus, the area of high shear forces moves along a path, controlled by the relative motion of the nozzle, such that the high shear forces gradually disperse powder particles into air. Preferably, the path begins just outside a point of contact between the high shear force area of flowing air and the border of the powder dose contour and follows the contour outline from the beginning until the end. Thus, the gradual de-aggregation and dispersal of a medication powder is an inherent essential characteristic of an Air-razor method.

Figure 6:
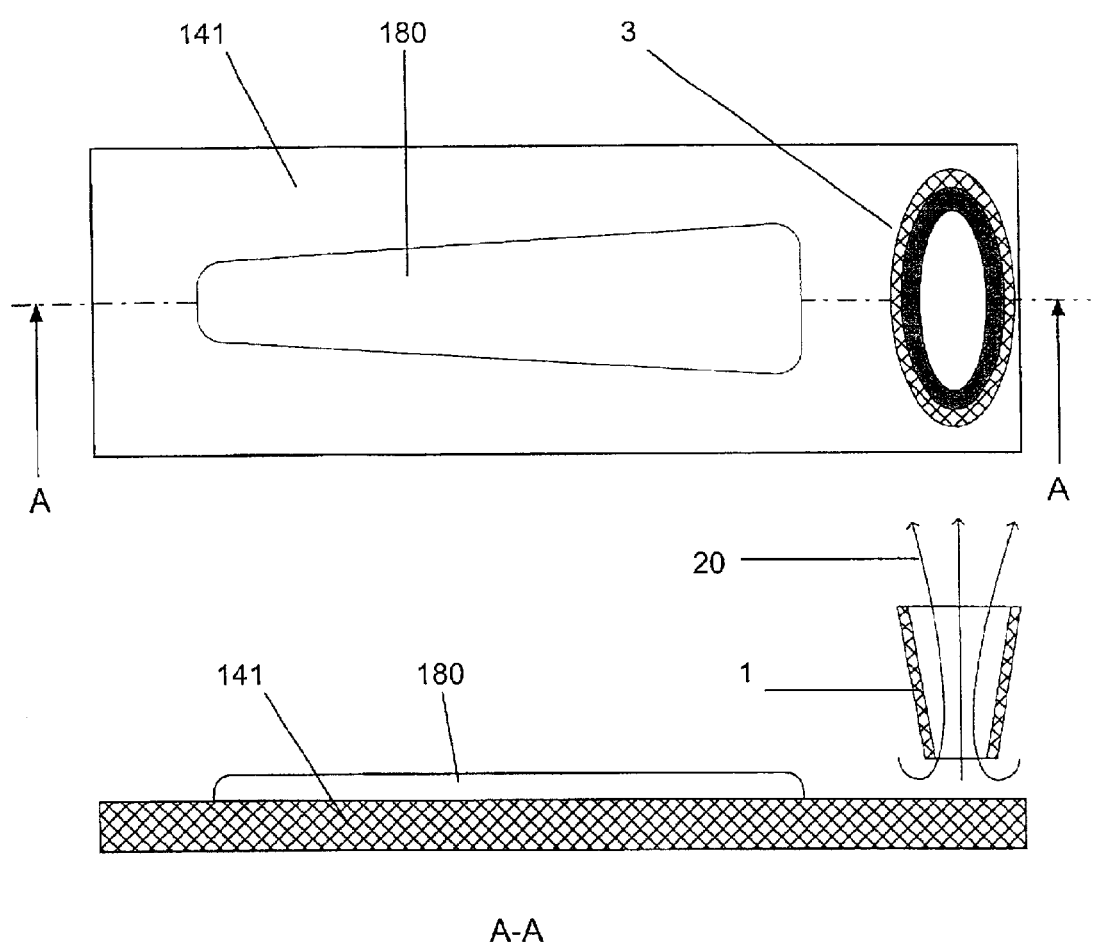
FIG. 6 illustrates a substrate member with a load of powder onto it and a nozzle with an elliptical inlet aperture.
Figure 7:
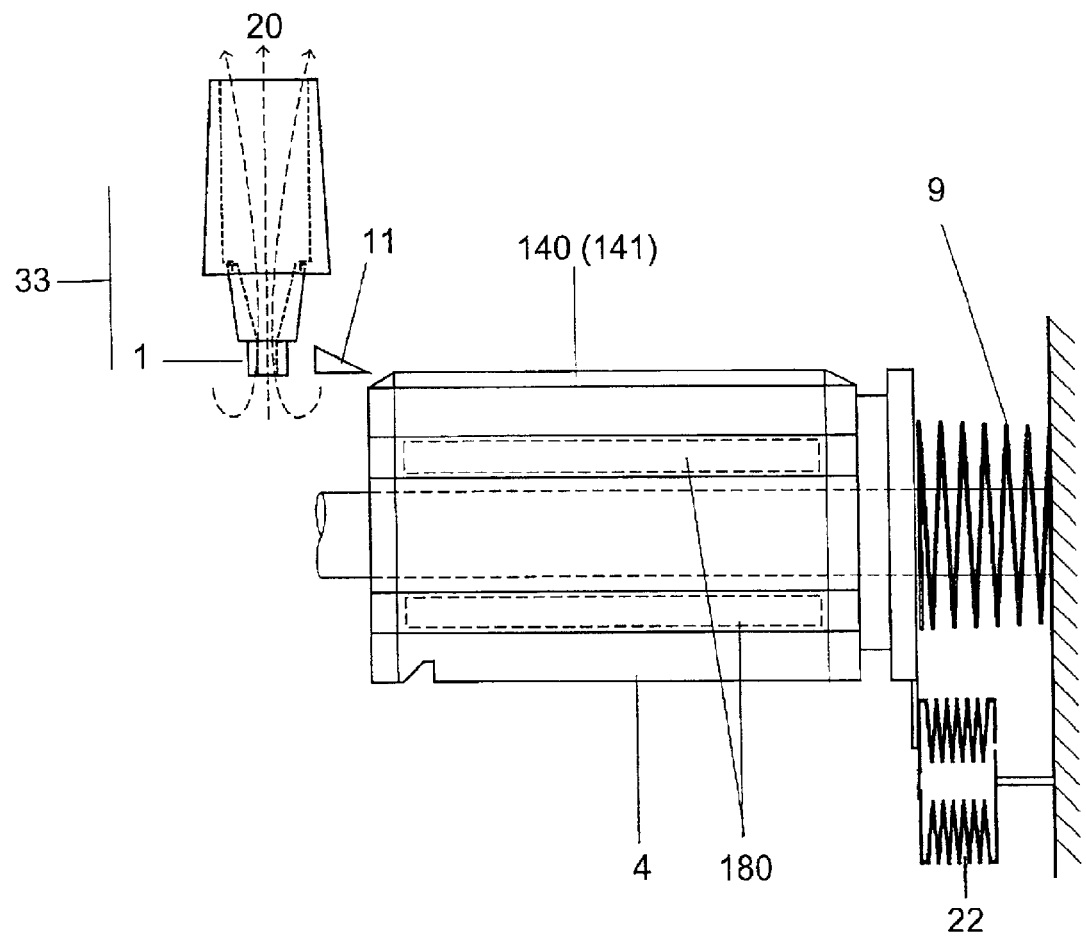
FIG. 7 illustrates an embodiment of a powder Air-razor device and a dosing member in a loaded state before release.
Figure 8:
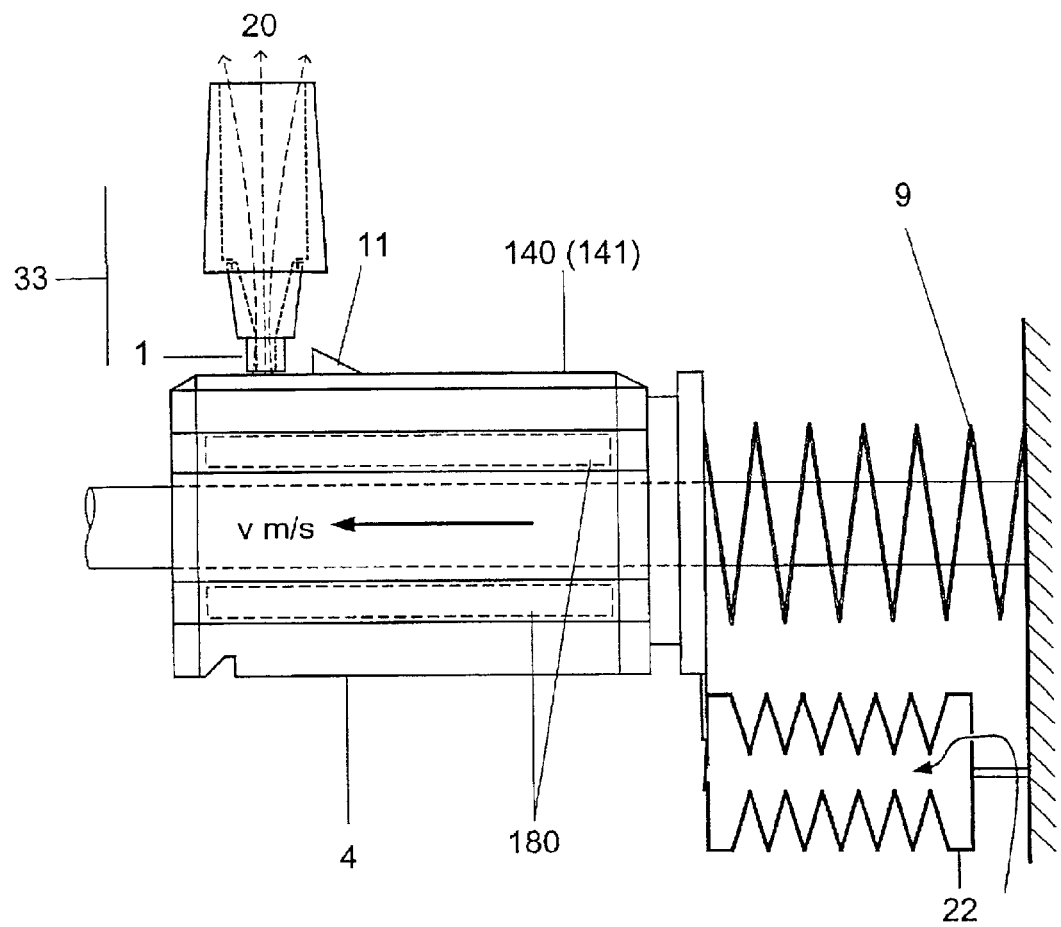
FIG. 8 illustrates an embodiment of a powder Air-razor device and a dosing member just after starting of a release of the powder dose.
Figure 10:
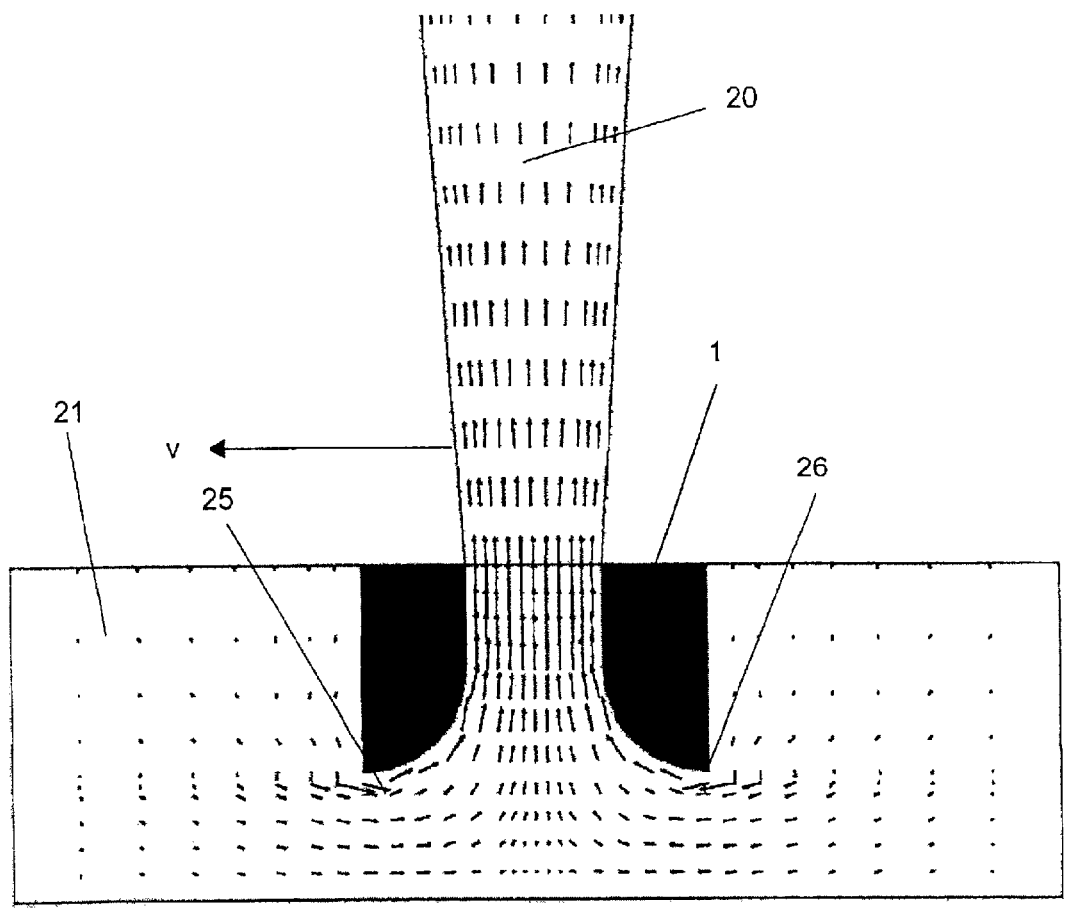
FIG. 10 illustrates an embodiment of a nozzle inlet opening and the air speed pattern developing during an applied suction effort.
Figure 11:
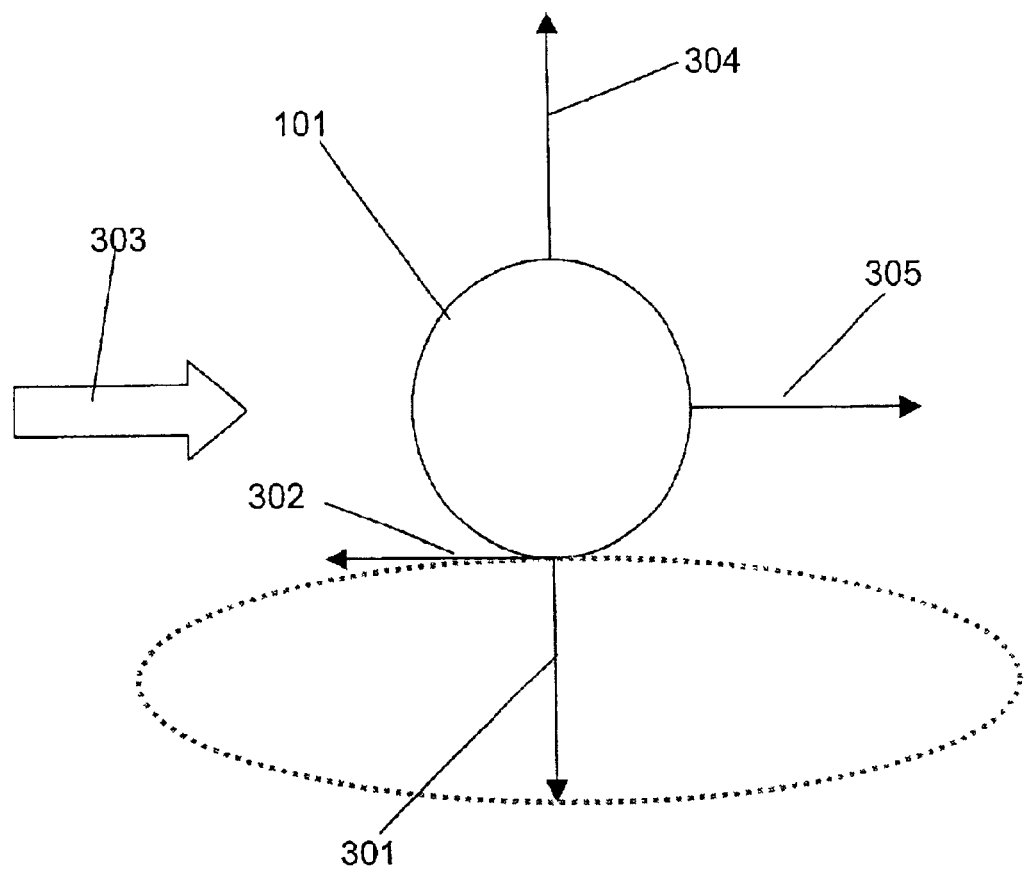
FIG. 11 illustrates the different forces acting on a stationary particle situated in a stream of air.

The area of high shear stress adjacent to a nozzle is illustrated in FIG. 10. FIG. 10 illustrates graphically the resulting air speed from a suction effort applied to the nozzle outlet as a function of coordinates in a plane perpendicular to a substrate member plane through the longitudinal centerline of the same, thus showing a cross section view of the nozzle 1. The air velocity is illustrated by a multitude of arrows pointing in the direction of the flow, the length of the arrows indicating the relative velocity of air at the point in question, thus showing how the air velocity varies with the position relative the nozzle aperture. The direction of the relative motion between the nozzle and powder load is indicated by the arrow "v". Still air 21 is gradually accelerated into an air stream 20 of 60 1/min, steady state, going into the nozzle and controlled by the suction. The resulting shear forces reach a maximum in the area designated 25. The illustration in FIG. 10 is an example of an embodiment of a nozzle. The area of the nozzle aperture may have different form 3 (see FIG. 6) for different applications, but a circular or elliptic shape is preferred. Likewise, the aperture wall thickness and curvature 26 may be given different forms depending on the application, since the form has a great influence on the flow pattern for the air being sucked into the nozzle.

Efficient Use of Energy

The dosing time interval for de-aggregation and dispersal of powder by an Air-razor may be selected, depending on the application within a time frame of an inhalation. Most prior art inhalers will use the inhalation power from the user during a short period only. This means that the total energy used for de-aggregation is correspondingly low in these inhalers, unless external de-aggregation energy is supplied. The time interval for an Air-razor delivery may e.g. be set to 1 second, which means that the inhalation power during this full second is used for de-aggregating particle aggregates.

$$E = \int_0^T P(t) \cdot dt$$

The total energy E equals the time integral of the power P over the entire period T, e.g. T=1 second.

Should the selected dosing time interval be too short, full entrainment of particles will not take place. The effect on a system comprising an Air-razor will be large-scale retention of powder onto the substrate member. A model is therefore needed for assessing the number of particles dispersed into air with time. One such model assumes that a fluctuating turbulent flow is acting on the particles. Some of the eddies will be strong enough to separate particles in an aggregate or from a surface. The successful eddies will occur with typical time intervals based on probability. Each eddy will set a fraction of the total particles free. If all particles experience the same adhesion force, the model holds true and the entrainment rate would typically follow an exponential curve. However, the adhesion force varies from particle to particle and some will stick harder than others will and the fraction of hard-sticking particles will increase with time. This slows down the release rate. Hence, a modified model has been suggested, which describes the rate of particle release as a 1/t-curve, where t represents time and so the total number of particles n dispersed in the airflow will typically follow its integral, a $\log_e$ (t)-curve, illustrated in FIG. 13. The curve describes the entrainment over a 'long time'. A significant fraction of the powder will also be released within a short time (typically 10 ms). The graph underlines the importance of using a moderate speed v between the nozzle and the powder envelope. Too high speed will give insufficient time on 'each spot' and thus leave a significant amount of powder undispersed, still onto the substrate member. Too low speed will jeopardize the objective of delivering the load of powder within a specified dosing time interval.

The preferred embodiments use substrate members to serve as carriers onto which medicament powders may be deposited in extended structures presenting suitable properties in terms of occupied area, powder envelope, particle size, mass, porosity, adhesion etc for de-aggregation and dispersal into air by the powder Air-razor device. The load of powder may or may not constitute a metered dose of the medicament in question. Substrate members are convenient means for making powders accessible to an Air-razor device, but other means exist, which should be obvious to a person skilled in the art. The degree of particle aggregation and powder porosity play an important role in achieving the best possible fine particle fraction and dispersal into air of the powder as it is forcibly entrained in air as a result of a release process. Finely divided medication powders with primary particle size below 10 $\mu$m are rarely free flowing, but to the contrary quite given to forming aggregates. Thus, finely divided powders that are less prone to forming aggregates and/or requiring less energy to break up formed aggregates are preferred in Air-razor applications. For example, ordered mixtures may be used to facilitate de-aggregation and dispersion into air of the active substances, which optionally may include pharmacologically acceptable excipients, used e.g. to dilute the active substance or, indeed, to improve one or more qualities of the active substance, such as bioavailability or electrostatic properties.

An example of a suitable powder for an Air-razor application is an electro-powder. Electro-powder is defined as a prepared dry powder medication substance with or without one or more excipients meeting a set of electrical specifications for optimum electrostatic dose forming properties. For further details, see our Swedish Patent No. SE 0002822-5, which is hereby incorporated herein by reference.

An example of a suitable dose of medication powder, formed onto a substrate member to be used in an Air-razor application, is an electro-dose. The term electro-dose, presented in our Swedish Patent No. SE 0003082-5, which is hereby incorporated herein by reference, refers to a dose of pre-metered medicament powder intended for use in a dry powder inhaler. The electro-dose is formed from an electro-powder comprising an active powder substance or a dry powder medicament formulation with or without one or more excipients, the electro-dose being formed onto a substrate member, which is part of a dosing member.

An example of a preferred method of forming a metered dose utilizes an electrostatic or electro-dynamic field deposition process or combinations thereof for depositing electrically charged particles of a medication powder onto a substrate member, such as an electrostatic chuck or a dosing member. The so formed electro-dose presents suitable properties in terms of occupied area, powder contour, particle size, mass, porosity, adhesion etc for easy de-aggregation and dispersal into air by the powder Air-razor device. However, in prior art, other methods of forming a load of powder exist, which are suitable for an Air-razor application e.g. mechanical, pneumatic or chemical methods. For example, doses may be produced by conventional volumetric or gravimetric metering methods, optionally followed by exposing the doses to a supply of energy. The purpose of supplying energy, e.g. by vibrating or giving the dose an energy impulse, would be to give the dose optimal spatial and porous qualities to be suitable for a power Air-razor application.

Figure 1B:
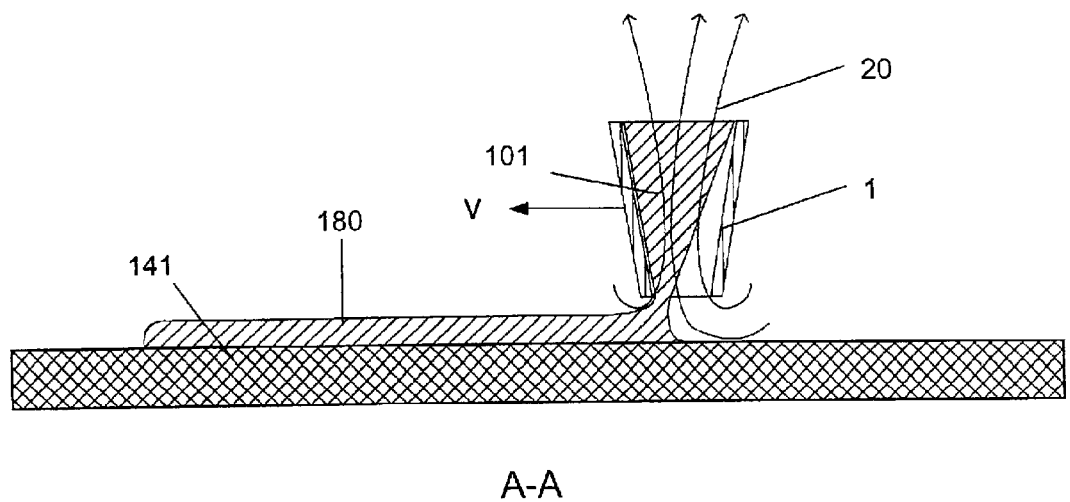

In a preferred embodiment, exemplified in FIGS. 1*a* and 1*b*, the powder Air-razor device involves the introduction of a controlled relative motion between a load of powder 180 deposited onto a substrate member 141 and a suitably arranged nozzle 1, which collects and directs a local high velocity stream of air 20. By pointing the nozzle inlet towards the contour of the powder load on the substrate element, the power of the air stream, resulting from the suction effort, acts as a powder Air-razor on the powder, de-aggregating and dispersing into air the particles 101 of the accessed powder on the substrate member. As the nozzle moves in the direction of the extended contour of the load of deposited powder, primary particles and particle aggregates are gradually accessed and subjected to the shearing stresses and inertia power of the air stream going into the nozzle inlet aperture. Thus, the powder Air-razor sequentially de-aggregates, releases, disperses and entrains individual particles into the air flowing into the nozzle.

In other embodiments of the powder Air-razor device the substrate member may be replaced by other devices or arrangements for implementing the necessary relative motion of a medicament powder in relation to the nozzle. It is for instance possible to arrange a vibrating element or a gravitation feeder, or a screw feeder or a conveyor feeder or a pneumatic tube feeder and similar devices for moving powder gradually from a powder store to a position where the powder may be accessed by the air stream going into the nozzle, thus achieving the powder Air-razor effect. The nozzle may remain stationary or moving relative to other elements, participating in the process of de-aggregation and dispersal of powder into air, but still the result of the process depends on the relative motion between powder and nozzle. A consequence of the high efficiency of the powder Air-razor is that a high proportion of available powder presented in advance of an inhalation is de-aggregated and dispersed into air, regardless of how the powder is presented i.e. if a substrate member serves as carrier for the powder or if powder is made available by other means. The accumulated mass of active medication particles in a load of powder dispersed into inhalation air by the Air-razor, may be de-aggregated by the Air-razor to at least 40% fire particle fraction (FPF) by mass based on the available active medication particles in the load of powder. Preferably, the Air-razor may be capable of de-aggregating said powder mass to at least 50% FPF and more preferably to at least 60% FPF. The definition of FPF in this context is the fraction of delivered active medication particles by mass with a maximum aerodynamic particle size of 5 $\mu$m.

The first objective for the Air-razor is to release individual fine particles into air i.e. to overcome the adhesive forces, such as van der Waal, electrostatic, gravity, friction etc, binding a particle to other particles in the aggregates of the powder and/or to the substrate surface. The second objective for the Air-razor is to direct all airborne particles into the nozzle with as few lost particles as possible. The particles entering the nozzle should then be transported entrained in air to the airways of a user by means of a suitably arranged fluid channel, which may not be part of the Air-razor. To fulfill the objectives the Air-razor needs a source of energy. Surprisingly, it has been found that the available drive power from the suction effort by the inhalation of a user provides ample energy for the operation of a powder Air-razor device. A normal inspiration effort by an adult user can be shown to produce a low-pressure approximately in a range 1–8 kPa. While a low-pressure in this range is usable, the preferred embodiment uses a range 1–4 kPa for ease of use by most people. Experiments have shown that the limited low-pressure, or drive pressure, thus produced may be used very efficiently, rendering external sources of power unnecessary in the inhalation process. Although a powder Air-razor works equally well with an external power source, which partially or completely supplies suction power, an external power source does not offer any benefits and is therefore superfluous, if the Air-razor is properly designed. However, the relative motion between powder and nozzle, necessary for the operation of an Air-razor, is preferably not powered by the inhalation effort, although this would be entirely possible.

Instead, the relative motion may be arranged in many different ways, including e.g. mechanisms comprising spring elements with a capacity for storing potential energy given by the user in handling the device.

The conclusions for an Air-razor device are:

1. Make the nozzle inlet opening flow efficient, such that as little energy of the available inhalation pressure drop as possible is lost. Instead, the pressure drop should be used to produce airflow of highest possible speed into the nozzle, thereby optimizing the shear stress and turbulence acting on the particles.
2. Introduce a relative motion between the powder and the nozzle. The relative speed should be chosen depending on the application, e.g. medication target area, dose size, type of patient etc, and not faster than making sure that all particles of the available powder are subjected to high air speeds, such that retention is kept low.

In line with the first conclusion, the present invention makes the use of baffles or other restrictions in the downstream flow path for creating turbulence, impaction and thereby de-aggregation superfluous, contrary to common solutions in prior art. The available energy for de-aggregation and dispersal is concentrated to areas around the nozzle inlet opening, leaving the interconnecting flow channels up to and including a mouthpiece with the single task of transporting the airborne particles to the user with a minimum of particle retention. By using the Air-razor device retention in the downstream flow path may therefore become substantially reduced, thus presenting an opportunity for delivering a very high share of the available powder load to the user and with an excellent FPF value.

In the context of the document, the term "adjacent to" is often used to describe the distance between the plane of a nozzle inlet opening and the plane of a surface of a substrate member or the top plane of the contour of a load of powder onto a surface of a substrate member. Normally these planes are parallel. For maximum Air-razor effect, it is advantageous if the distance from the nozzle inlet plane to the load of powder, which is going to be sucked up by the air stream into the nozzle, is shorter than a millimeter. Depending on the design of the inhaler where the Air-razor device and/or arrangement is implemented, manufacturing tolerances and other factors will influence the decision where the nozzle should be positioned relative to the substrate member or the powder load.

The teaching of the invention is unaffected by which mechanisms are deployed to bring about the relative motion between the members involved. Thus, it is immaterial for the present invention if the nozzle is the moving part and the substrate member is stationary or vice versa or if a combination of nozzle/substrate motions relative yet another fixed or moving element is used. In a preferred embodiment, see FIG. 6, the entrance aperture 3 of the nozzle 1 is shaped in an elliptical or slit-like fashion, such that the aperture is sufficiently wide to cover the width of the area occupied by powder 180 on the substrate 140. Relatively speaking, in a preferred embodiment the nozzle describes a motion from a start position to an end position, traversing across all of the occupied area of the powder in one stroke. Advantageously, the start position of the nozzle is outside the occupied area by a distance "s" ($s \geq 0$+size of aperture) to allow the suction-initiated airflow to build up through the nozzle to a point before the relative motion brings the nozzle adjacent to the powder. In such a preferred embodiment, the power and shearing stress of the powder Air-razor is established before it approaches the powder contour and begins to attack particle aggregates of the powder. A further improvement of the powder Air-razor device is the introduction of a suction related triggering of the flow into the nozzle, such that the resulting air speed is sufficiently high to generate the necessary powder Air-razor effect. In a preferred embodiment, the aperture of the nozzle is brought in close proximity to the substrate member and may even contact it, although generally not contact the load of powder onto the substrate member. Dependening on the dose contour, e.g. if the dose is disturbed prior to the inhaltion cycle, the nozzle may contact some of the powder in the dose during delivery without any significant degradation of the Air-razor performance, e.g. regarding de-aggregation and dispersal efficiency. In other embodiments, the relative motion between substrate member and nozzle may comprise more steps than one, which may be arranged in a discontinuous pattern. E.g. a pattern may be devised to let a nozzle with a smaller aperture cover the occupied area of the powder by traversing more than once across different parts of the powder area, covering a small area of the total aggregated area of the powder each time. The particles 101 thus cut free sequentially and de-aggregated from the particle aggregates by the powder Air-razor, are rapidly entrained in the air stream going into the nozzle.

In contrast, many prior art inhaler devices begin the powder release cycle by introducing the powder in the channel connecting the air inlet and the final mouthpiece air outlet. The powder is thus surrounded by a volume of stationary air. This considerable volume of air is then accelerated by the suction effort, normally provided by a user, sometimes boosted by added external energy, e.g. by vibrating the medicament powder or giving it an extra puff of pressurized air. All of the powder is subjected to this treatment at the same moment resulting in unsatisfactory de-aggregation of the total powder mass entrained in the air. In short, this means poor efficacy, because not all of the powder is subjected to the necessary shearing stress level for de-aggregation to really happen. Further, because the speed of air surrounding the powder is zero when the release process begins, some of the particle aggregates in the powder will be torn loose during the acceleration phase when the shearing stress of the airflow is not strong enough to de-aggregate the aggregates and accordingly they are delivered as intact aggregates. Within published specification limits, the present invention of a powder Air-razor discloses that all of the powder, which is accessed by the moving nozzle, is indeed subjected to the necessary shearing stress to be de-aggregated.

Figure 2A:
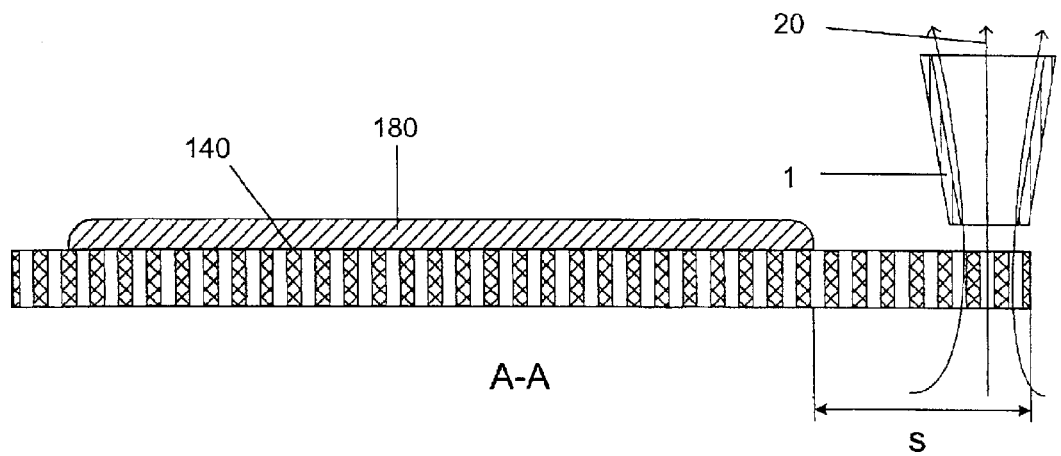
Figure 2B:
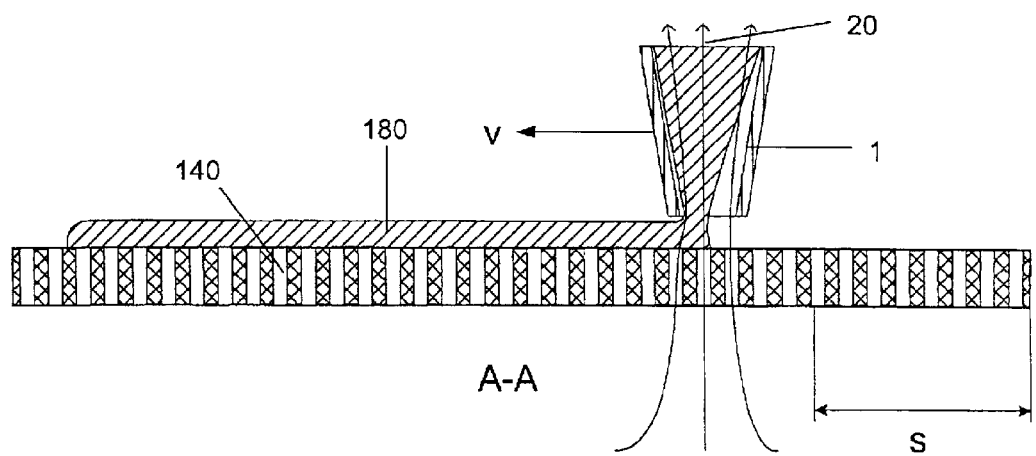
Figure 3A:
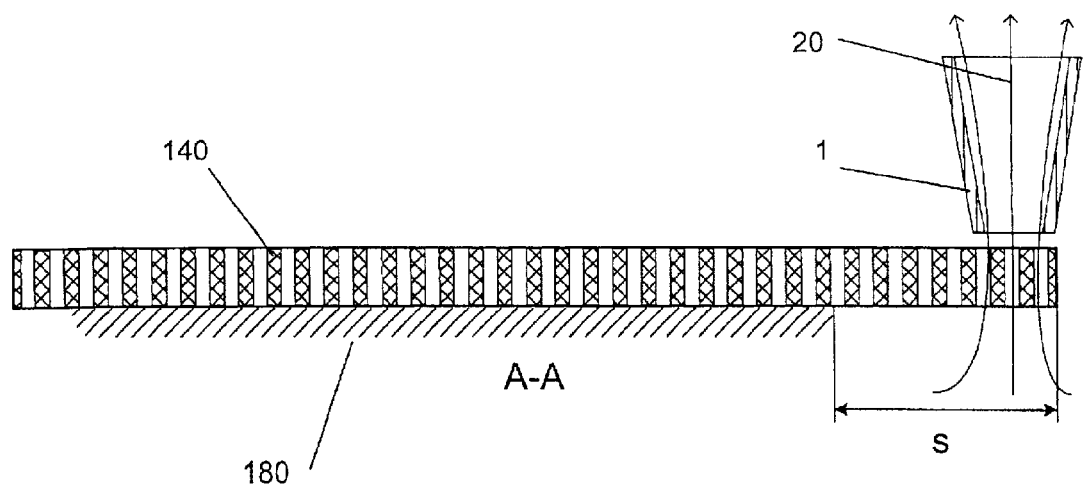
Figure 3B:
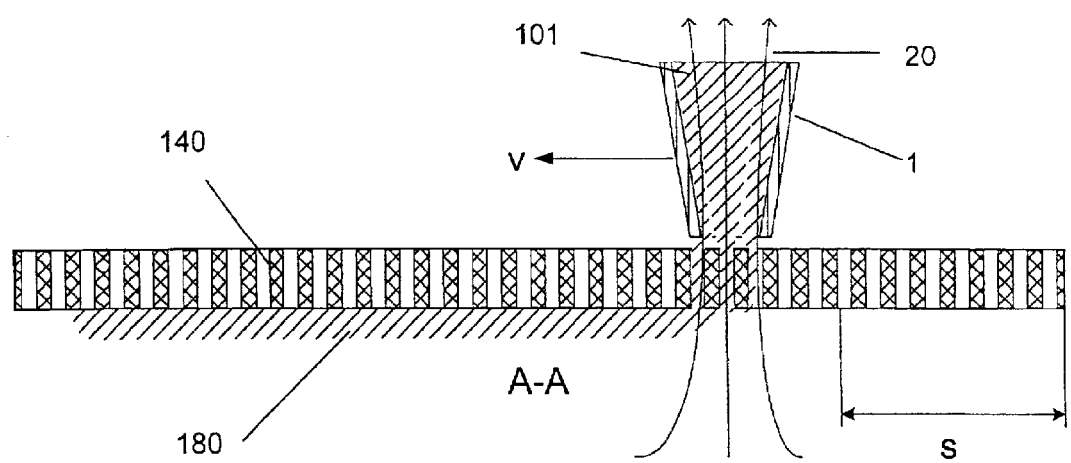

Interestingly, tests have shown that there are no distinct performance differences between a perforated substrate member 140 and a non-perforated substrate member 141 when used in an Air-razor application. In the case of a non-perforated substrate member, the nozzle must be positioned adjacent to the powder and at the same side of the substrate member as the powder, illustrated in FIG. 1b. The air stream 20 enters into the nozzle from the sides, to thereby cut particles 101 loose from the load of powder 180 in the process. On the other hand, if a perforated substrate member 140 is used, the de-aggregation and dispersal may be facilitated by air passing through the perforations and further through the load of powder 180 before the air stream 20 passes into the nozzle 1, see FIG. 2b. A further improvement of the de-aggregation and dispersal may be attained from a perforated substrate member, if the nozzle may be positioned at the opposite side to the powder of the substrate member, such that the air stream hits the powder first before continuing through the perforations, and then into the nozzle inlet aperture, see FIG. 3b. Theoretically, a perforated substrate member may offer better FPF results compared to a non-perforated substrate member, all other parameters being equal, because the shearing forces experienced by the powder on the perforated substrate member may be better distributed in the part of the powder where the air flow attacks at any given moment of the suction. The predominant airflow goes straight through the powder via the perforations or vice versa and into the nozzle rather than making a 90°–180° turn round the nozzle inlet periphery as in the case of the non-perforated substrate member. On average, a higher proportion of the powder is thus subjected to strong shearing forces, if the substrate member is perforated. In practice, however, what type of substrate member to use depends on the application, since the difference in performance for the Air-razor applied to a non-perforated or perforated substrate member has been seen to be quite small.

Figure 4A:
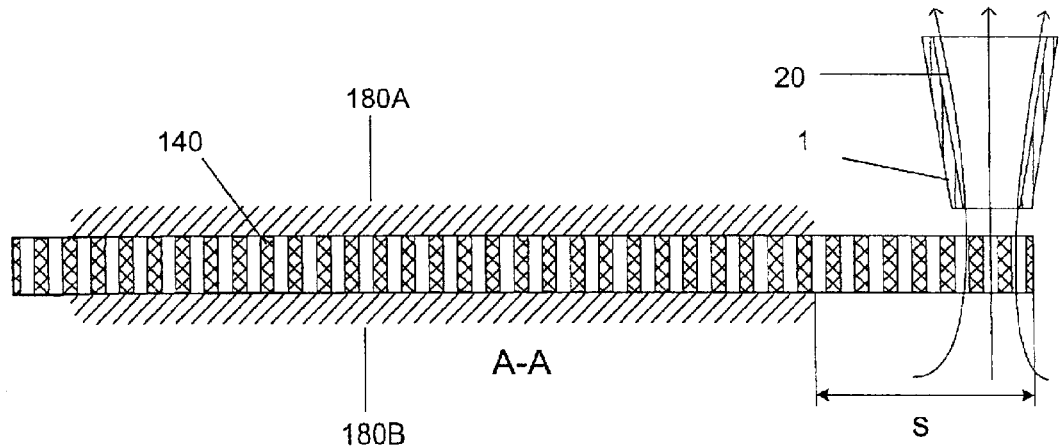
Figure 4B:
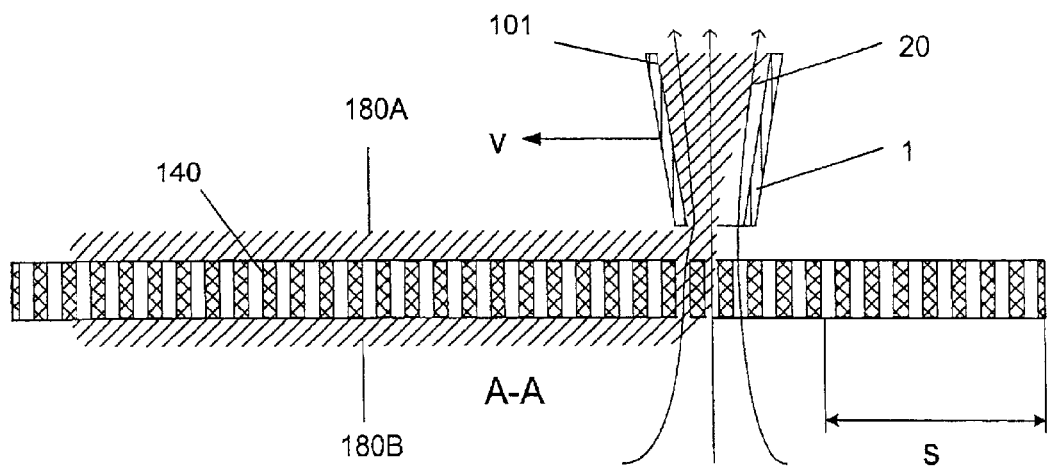
Figure 5:
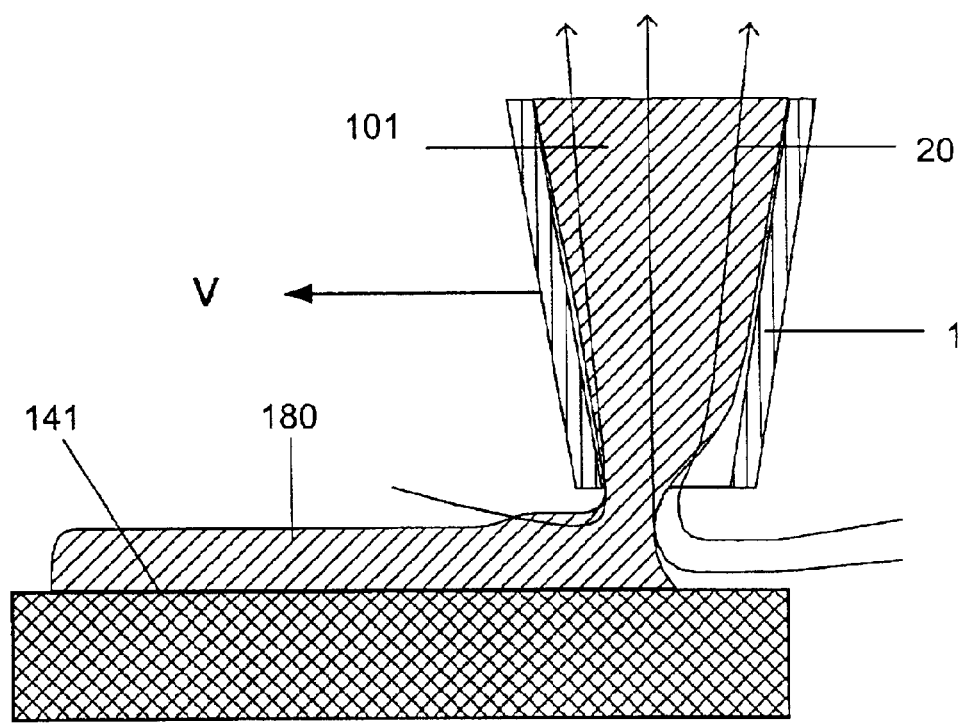
FIG. 5 illustrates a medication powder being released, de-aggregated, dispersed and entrained in air by a powder Air-razor device.

Yet other embodiments of a perforated substrate member may position the nozzle on the same side of the substrate member as the medicament powder. Positioning the nozzle so that it may move close to the powder but preferably not in contact with it offers a possibility of forming e.g. a part-dose on both sides of the substrate member, as illustrated in FIGS. 4a and 4b. In such a case the two part-doses 180A and 180B will preferably be delivered in the same way as described above, only that the part-dose on the substrate member side opposite to the nozzle, termed 180B, will be sucked through the perforations to become mixed with the other dose, termed 180A. A possible application for forming part-doses on both sides of the substrate member may be in cases where two medicaments are incompatible to mix, but need to be administered at the same time to a user.

TEST EXAMPLES

In order to study the differences in fine particle fraction in the delivered dose to a user between a stationary nozzle and an Air-razor during release of the dose, the following in vitro experiment was performed, using a finely divided lactose powder comprising 85% by mass of particles with a primary particle size less than 3 $\mu$m:

A. Stationary Nozzle

A number of 30 spot-like doses of lactose, about 3 mm in diameter, with mass approximately 70 $\mu$g each were formed on a 150 mesh (150 stitches per inch) metal wire net serving as a substrate member. The substrate member was then positioned adjacent to a nozzle with its inlet at the opposite side of the substrate member to that of the dose. The area of the nozzle opening was somewhat larger than the dose. The nozzle outlet was connected to an Anderson impactor. The suction was then as quickly as possible brought up to a pressure drop of 2 kPa resulting in air speed 33.4 liters per minute. The dose was dispersed in the air stream going into the nozzle and delivered into the impactor. The release procedure was repeated for all 30 doses, total mass approximately 2 mg. The powder of the doses settled in the steps of the impactor. The particle distribution of the delivered mass in the various steps of the impactor is shown in Table 1. Retention in the nozzle connected to the impactor was determined to 54 $\mu$g. All masses were determined by a HPLC method.

The fine particle fraction, smaller than 5 $\mu$m, was determined by interpolation between steps 2 and 3 to 17.1% of the delivered mass and 16.7% of total determined mass.

TABLE 1

| Anderson Impactor | Flow-corrected particle cut-off size $\mu$m | Measured mass by HPLC $\mu$g | Distribution in each step of impactor % | Cumulative distribution in impactor % |
|---|---|---|---|---|
| Preimpactor |  | 1337 | 66.9 | 100 |
| Step 0 | 9.20 | 139 | 6.9 | 33 |
| Step 1 | 8.28 | 144 | 7.2 | 26 |
| Step 2 | 5.34 | 123 | 6.1 | 19 |
| Step 3 | 4.33 | 132 | 6.6 | 13 |
| Step 4 | 3.04 | 37 | 1.8 | 6 |
| Step 5 | 1.93 | 10 | 0.5 | 4.5 |
| Step 6 | 1.01 | 4 | 0.2 | 4 |
| Step 7 | 0.64 | 4 | 0.2 | 4 |
| Filter | 0.37 | 71 | 3.6 | 3.6 |
| Total |  | 2000 |  |  |

B. Air-razor Applied to a Perforated Substrate Member

The arrangement was prepared such that 10 doses from the same batch of lactose as in A. were formed as 15 mm long, 3 mm wide strips on the same type as in A. of 150 mesh (150 stitches per inch) metal wire net serving as substrate members. The net was then positioned adjacent to the same nozzle as before with its inlet at the opposite side of the net to that of the dose, but some distance sideways removed from the area occupied by the dose. The diameter of the nozzle opening was somewhat larger than the dose width.

The nozzle was a part of the same measuring arrangement as before. The same Anderson impactor was used as before. The difference now was that the suction, 2 kPa, was applied first and the air flow was allowed to stabilize, before the net (in this case) was moved past the nozzle parallel to the dose strip, such that the dose was gradually sucked up by the flowing air going into the nozzle and delivered into the impactor. The release procedure was repeated for all 10 doses, total mass approximately 2.6 mg. The particle distribution of the delivered mass in the various steps of the impactor is shown in Table 2. Retention in the nozzle connected to the impactor was determined to 256 $\mu$g. The masses were determined by a HPLC method as before.

TABLE 2

| Anderson Impactor | Flow-corrected particle cut-off size μm | Measured mass by HPLC μg | Distribution in each step of impactor % | Cumulative distribution in impactor % |
|---|---|---|---|---|
| Preimpactor | — | 432 | 16.6 | 100.0 |
| Step 0 | 9.19 | 67 | 2.6 | 83.4 |
| Step 1 | 8.27 | 184 | 7.1 | 80.8 |
| Step 2 | 5.33 | 311 | 11.9 | 73.8 |
| Step 3 | 4.32 | 952 | 36.6 | 61.8 |
| Step 4 | 3.03 | 468 | 18.0 | 25.2 |
| Step 5 | 1.93 | 151 | 5.8 | 7.2 |
| Step 6 | 1.01 | 14 | 0.6 | 1.4 |
| Step 7 | 0.64 | 13 | 0.5 | 0.9 |
| Filter | 0.37 | 10 | 0.4 | 0.4 |
| Total | | 2602 | | |

The fine particle fraction, smaller than 5 μm, was determined by interpolation between steps 2 and 3 to 70.1% of the delivered mass and 63.8% of total determined mass.

C. Air-Razor Applied to a Non-perforated Substrate Member

A sample was taken from a series of doses of lactose, of the same batch of lactose as in the earlier experiments A. and B. Each dose was formed onto a non-perforated substrate member, the dose approximately a 15 mm long, 3 mm wide strip of powder. The selected sample dose was then positioned adjacent to the same nozzle with its inlet at the same side of the substrate member as the dose, but some distance sideways removed from the area occupied by the dose. The diameter of the nozzle opening was somewhat larger than the dose width.

The nozzle was a part of the same measuring arrangement as before. The same Anderson impactor was used as before. The suction, in this case 4 kPa, was applied first and the air-flow was allowed to stabilize, before the substrate member (in this case) was moved past the nozzle parallel to the dose strip, such that the dose was gradually sucked up by the flowing air going into the nozzle and delivered into the impactor. The particle distribution of the delivered mass in the various steps of the impactor is shown in Table 3. Retention in the nozzle connected to the impactor was determined to 74.3 μg. The masses were determined by a HPLC method as before.

The fine particle fraction, smaller than or equal to 5 μm, was determined by interpolation between steps 1 and 2 to 83.7% of the delivered mass and 72.0% of total determined mass. It is to be noted that the pressure in this case was 4 kPa compared to 2 kPa in the two earlier experiments. The results are therefore not directly comparable, but the test pressures are within the preferred range of 1–4 kPa.

TABLE 3

| Anderson Impactor | Flow-corrected particle cut-off size μm | Measured mass by HPLC μg | Distribution in each step of impactor % | Cumulative distribution in impactor % |
|---|---|---|---|---|
| Neck | — | 23 | 5.0 | 100.0 |
| Preimpactor | — | 12 | 2.6 | 95.0 |
| Step 0 | 8.33 | 12 | 2.5 | 92.4 |
| Step 1 | 7.50 | 31 | 6.7 | 89.9 |
| Step 2 | 4.83 | 72 | 15.7 | 83.1 |
| Step 3 | 3.91 | 136 | 29.6 | 67.4 |
| Step 4 | 2.75 | 78 | 17.0 | 37.8 |
| Step 5 | 1.75 | 28 | 6.2 | 20.8 |
| Step 6 | 0.92 | 10 | 2.3 | 14.6 |
| Step 7 | 0.58 | 9 | 2.0 | 12.3 |
| Filter | 0.33 | 47 | 10.3 | 10.3 |
| Total | | 459 | | |

The evidence of the experiments supports the claimed benefits for the inventive step of gradual de-aggregation and dispersal into air by introducing a relative motion between a nozzle and a medication powder. Using the shearing stress near the nozzle inlet periphery and the impact of the streaming air to full potential onto a boundary part of the medication powder contour, achieve a very high degree of de-aggregation and high fine particle fraction in the particles dispersed into air. The relative motion between nozzle and powder means a gradual approach to the powder by the shearing forces making release of a considerable load of powder possible. The experiments show that the Air-razor applied to a load of powder onto a non-perforated substrate member may give a very good performance, as does the Air-razor applied to powder onto a perforated substrate member. By optimizing the adhesion force between particles and between particles and substrate in the deposited powder, by optimizing the powder area, by optimizing the nozzle geometry and by optimizing the speed of the relative motion between nozzle and powder, de-aggregation and fine particle fraction, smaller than or equal to 5 μm, is pushed very close to 100% of the mass of the available medication powder.

In a preferred embodiment the speed "v" of the relative displacement powder load—nozzle in FIGS. 1b, 2b, 3b, 4b and 5 is controlled by suitable means, an element of which may be an air inlet valve, which opens when the pressure differential from the suction is suitably strong. Then, the resulting airflow quickly reaches the speed necessary for the powder Air-razor to efficiently de-aggregate and disperse into air the particles of the powder. To minimize flow losses as much as possible the nozzle and the downstream connecting channel may be given a conical shape such that the outlet area is larger than the inlet area. Controlling "v" implicates that a most suitable dosing time interval may be defined during which delivery of a load of powder should take place. The dosing time interval depends on several factors, e.g. targeted area of the airways, nominal powder load mass and type of user for the medication. From a starting point to an ending point the relative motion of powder versus nozzle must embrace the defined time interval, which normally is in a range of 0.01 to 5 seconds. The timing should be suitably selected for the application i.e. the points in time where the motion begins and ends within a time frame of a suction of air that is taking place.

Figure 9:
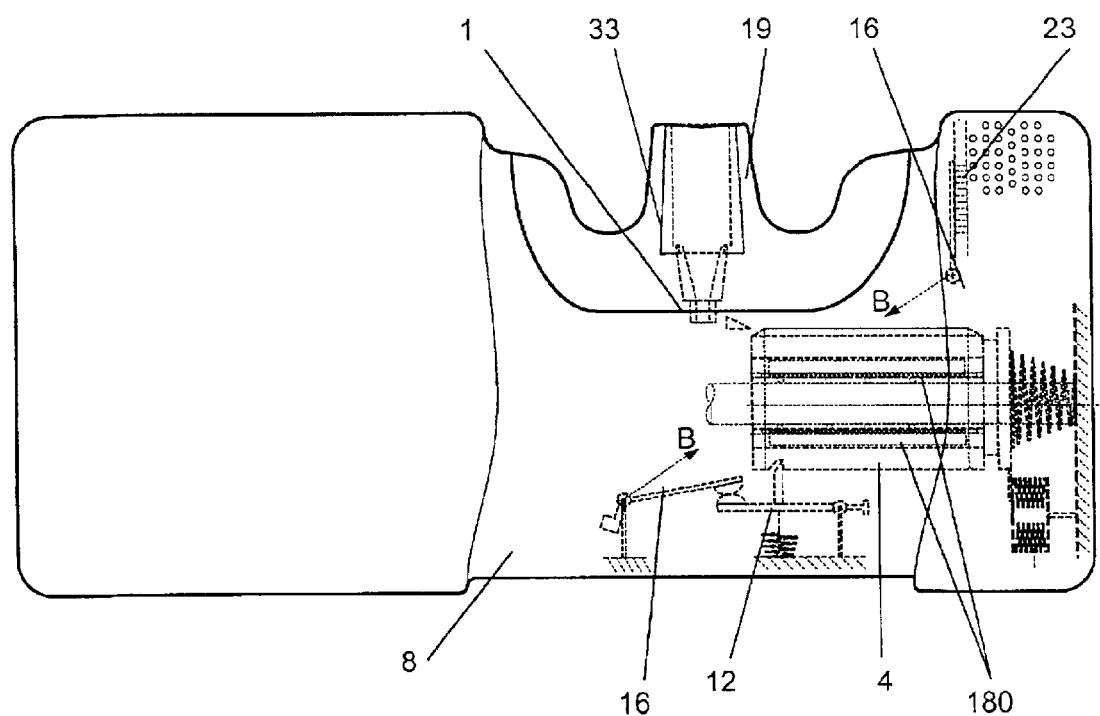
FIG. 9 illustrates an embodiment of an inhaler comprising a powder Air-razor device and a dosing member.

It is therefore important to optimize the delivery of the dose by means of a new type of inhaler device, which takes full advantage of the powder Air-razor device. An embodiment of such a new inhaler device is disclosed in FIG. 9.

What is claimed is:

1. A device for de-aggregating and into air dispersing particles of a finely divided dry medication powder loaded onto a substrate member, the powder made available for inhalation by means of a dry powder inhaler, wherein the device, referred to as a powder Air-razor, has a nozzle with a nozzle outlet and a nozzle inlet and a nozzle inlet aperture positioned adjacent to the available powder;

a suction of air, when applied to the nozzle outlet, creates a local, high velocity air stream into said nozzle inlet aperture and out through said nozzle outlet;

a relative motion, when introduced between the nozzle and powder onto the substrate member, is arranged such that the nozzle inlet, and the local, high velocity air stream going into the nozzle inlet aperture, traverses the available medication powder, thereby amounting to a powder Air-razor in releasing and dispersing the powder;

particle aggregates within the finely divided medication powder are de-aggregated by being subjected to shearing stresses, inertia and turbulence of air in the local, high velocity air stream going into said nozzle inlet aperture, whereby the particles of the finely divided medication powder are gradually dispersed into the air as available powder is gradually accessed by the local, high velocity air stream of the powder Air-razor when the nozzle and the powder are moved in relation to each other.

2. The device according to claim 1, wherein at least 40% of the medication powder mass loaded onto said substrate member is dispersed as fine particles in the inhaled air stream leaving the nozzle, said fine particles having an aerodynamic diameter equal to or less than 5 $\mu$m.

3. The device according to claim 1, wherein an area of the nozzle inlet is of the same order as, or smaller than an aggregate area occupied by the finely divided dry medication powder onto the substrate member; and said relative motion of the nozzle is arranged such that the nozzle inlet covers the aggregate area occupied by the finely divided dry medication powder in one or more traversing steps.

4. The device according to claim 1, wherein an aperture curvature of said nozzle inlet is given a suitable shape providing a best possible compromise between an objective of achieving maximum shear stress in the airflow into the nozzle inlet and an objective of minimizing particle loss due to retention in the nozzle.

5. The device according to claim 1, wherein the finely divided dry medication powder loaded onto said substrate member in order to be released constitutes a metered dose.

6. The device according to claim 1, wherein a timing for said relative motion of the nozzle is adjustable within a time frame of the suction of air taking place.

7. The device according to claim 1, wherein a time interval in a range of 0.01 to 5 s for said relative motion of the nozzle is pre-defined from a start position to an end position within a time frame of the suction of air taking place.

8. The device according to claim 1, wherein a usable pressure drop by the suction of air is in a range of 1–8 kPa and more preferably in a range of 1–4 kpa.

9. The device according to claim 1, wherein at least one finely divided medication powder is loaded onto a first or a second side or onto both sides of said substrate member.

10. The device according to claim 9, wherein the finely divided medication powder loaded onto a first and second side of said substrate member comprises a first medication powder onto the first side of the substrate member and a second, different medication powder onto the second side of the substrate member.

11. The device according to claim 9, wherein said substrate member is porous or perforated, such that the nozzle, if positioned at the first side, can suck powder, if present, off the first side and powder, if present, on the second side off the second side through pores or perforations of the substrate member, such that powder from the first and the second side, if available on either or both sides, will get sucked into the nozzle by the suction of air.

12. The device according to claim 1, wherein a defined level of low-pressure from the suction is required to trigger an air-flow into the nozzle, thereby ensuring that the resulting air speed is sufficiently high to generate a necessary powder Air-razor effect.

13. A device for de-aggregating and dispersing into air particles of a finely divided dry medication powder deposited in an electrostatic or electro-dynamic field deposition process, or combinations thereof, onto a substrate member, an individual amount of powder being intended for inhalation by means of a dry powder inhaler, wherein the device, referred to as a powder Air-razor, has a nozzle with a nozzle outlet and a nozzle inlet and a nozzle inlet aperture positioned adjacent to the individual amount of powder;

a suction of air, when applied to the nozzle outlet, creates a local, high velocity air stream into the nozzle inlet aperture and out through the nozzle outlet;

a relative motion introduced between the nozzle and powder onto the substrate member, is arranged such that the nozzle inlet and the local, high velocity air stream going into the nozzle inlet aperture, traverse the individual amount of medication powder, thereby amounting to a powder Air-razor in releasing and dispersing the powder;

particle aggregates within the finely divided medication powder are de-aggregated by being subjected to shearing stresses, inertia and turbulence of air in the local, high velocity air stream going into the nozzle inlet aperture, whereby the particles of the finely divided medication powder are gradually dispersed into the air as the individual amount of powder is gradually accessed by the local, high velocity air stream of the powder Air-razor when the nozzle and the powder are moved in relation to each other.

14. The device according to claim 13, wherein at least 40% of the medication powder mass loaded onto the substrate member is dispersed as fine particles in the inhaled air stream leaving the nozzle, said fine particles having an aerodynamic diameter equal to or less than 5 $\mu$m.

15. The de-aggregating and dispersing device according to claim 13, wherein an area of the nozzle inlet is of the same order as, or smaller than an aggregate area occupied by the medication powder onto the substrate member;

the relative motion of the nozzle being arranged such that the nozzle inlet will cover the aggregate area occupied by the finely divided dry medication powder in one or more traversing steps.

16. The device according to claim 13, wherein the finely divided dry medication powder loaded onto the substrate member in order to be released constitutes a metered dose.

17. The device according to claim 13, wherein a timing for the relative motion of the nozzle is adjustable within a time frame of the suction of air taking place.

18. The device according to claim 13, wherein a time interval in a range of 0.01 to 5 s for the relative motion of the nozzle is pre-defined from a start position to an end position within a time frame of the suction of air taking place.

19. The device according to claim 13, wherein a usable pressure drop by the suction of air is in a range of 1–8 kPa and more preferably in a range of 1–4 kpa.

20. The device according to claim 13, wherein at least one finely divided medication powder is deposited onto a first or a second side or onto both sides of the substrate member.

21. The device according to claim 20, wherein the finely divided medication powder deposited onto a first and second side of the substrate member comprises optionally different medicament powders, a first medication powder onto the first side of the substrate member and a second medication powder onto the second side of the substrate member.

22. The device according to claim 20, wherein the substrate member is porous or perforated, such that the nozzle, if positioned at the first side, can suck powder, if present, off the first side and powder, if present, on the second side off the second side through pores or perforations of the substrate member such that powder from the first and the second side, if available on either or both sides, will get sucked into the nozzle by the suction of air.

23. The device according to claim 13, wherein a defined amount of low-pressure from the suction is required to trigger an air-flow into the nozzle, thereby ensuring that the resulting air speed is sufficiently high to generate a necessary powder Air-razor effect.

24. An arrangement for de-aggregating and into air dispersing particles of a finely divided dry medication powder, comprising a nozzle having a nozzle inlet and a nozzle outlet and a finely divided dry medication powder made available for a release, the powder being intended for inhalation by means of a dry powder inhaler, wherein a suction of air is applied to the nozzle outlet, thus creating a local, high velocity air stream into a nozzle inlet aperture and out through the nozzle outlet;

a relative motion, when introduced between the nozzle and powder, is arranged such that the powder is made available adjacent to the nozzle inlet gradually, while suction is still applied, thus making the local high velocity air stream release and disperse the powder gradually;

particle aggregates within the finely divided medication powder are de-aggregated by being subjected to shearing stresses, inertia and turbulence of air in the local, high velocity air stream going into the nozzle inlet aperture, whereby the particles of the finely divided medication powder are gradually dispersed into the air as available powder is gradually accessed by the local, high velocity air stream when the nozzle and an amount of powder are moved in relation to each other.

25. The arrangement according to claim 24, wherein the arrangement comprises an Air-razor device.

26. The arrangement according to claim 24, wherein at least 40% of the available powder mass is dispersed as fine particles in the inhaled air stream leaving the nozzle, said fine particles having an aerodynamic diameter equal to or less than 5 $\mu$m.

27. The arrangement according to claim 24, wherein the finely divided dry medication powder made available for a release constitutes a metered dose.

28. The arrangement according to claim 24, wherein the finely divided dry medication powder is made available for a release by means of a moving substrate member or a vibrating element or a gravitation feeder, or a screw feeder or a conveyor feeder or a pneumatic tube feeder.

29. The arrangement according to claim 24, wherein a timing for the relative motion of the nozzle is adjustable within a time frame of the suction of air taking place.

30. The device according to claim 24, wherein a time interval in a range of 0.01 to 5 s for the relative motion of the nozzle is pre-defined from a start position to an end position within a time frame of the suction of air taking place.

31. The arrangement according to claim 24, wherein a usable pressure drop by the suction effort is set in a range of 1–8 kPa and more preferably in a range of 1–4 kPa.

32. The arrangement according to claim 24, wherein a defined amount of low-pressure from the suction is required to trigger an air-flow into the nozzle, thereby ensuring that the resulting local, high velocity air speed is sufficiently high to generate a necessary powder Air-razor effect.

* * * * *